United States Patent [19]
Todd

[11] 3,983,879
[45] Oct. 5, 1976

[54] SILICONE CATHETER
[75] Inventor: Donald A. Todd, Elk Grove Village, Ill.
[73] Assignee: Western Acadia, Incorporated, Chicago, Ill.
[22] Filed: June 23, 1975
[21] Appl. No.: 589,553

Related U.S. Application Data
[62] Division of Ser. No. 491,623, July 25, 1974, Pat. No. 3,926,705.

[52] U.S. Cl. ............................................. 128/349 B
[51] Int. Cl.² ........................................ A61M 25/00
[58] Field of Search .......... 128/348, 349 B, 349 BV, 128/350 R, 351, 325, 344, 246

[56] References Cited
UNITED STATES PATENTS

| | | |
|---|---|---|
| 3,292,627 | 12/1966 | Harautuneian .................. 128/349 B |
| 3,426,758 | 2/1969 | Harautuneian .................. 128/349 B |
| 3,544,668 | 12/1970 | Dereniuk ...................... 128/349 B X |
| 3,884,242 | 5/1975 | Bazell et al .................. 128/349 B X |

FOREIGN PATENTS OR APPLICATIONS

| | | | |
|---|---|---|---|
| 693,224 | 6/1953 | United Kingdom ............. | 128/349 B |

Primary Examiner—Dalton L. Truluck
Attorney, Agent, or Firm—Dennison, Dennison, Meserole & Pollack

[57] ABSTRACT

An improved catheter comprising a tubular body portion comprising a primary lumen and an inflation lumen and an outer covering, a portion of which is inflatable to form an anchoring bubble, wherein a layer of thermoplastic material is applied around the tubular catheter body in the region underlying the anchoring bubble, the thermoplastic layer containing a hole through which an inflation medium can be injected from the inflation lumen to expand a portion of the outer covering to form the anchoring bubble and the thermoplastic layer being composed of a material to which the outer covering does not adhere.

5 Claims, 5 Drawing Figures

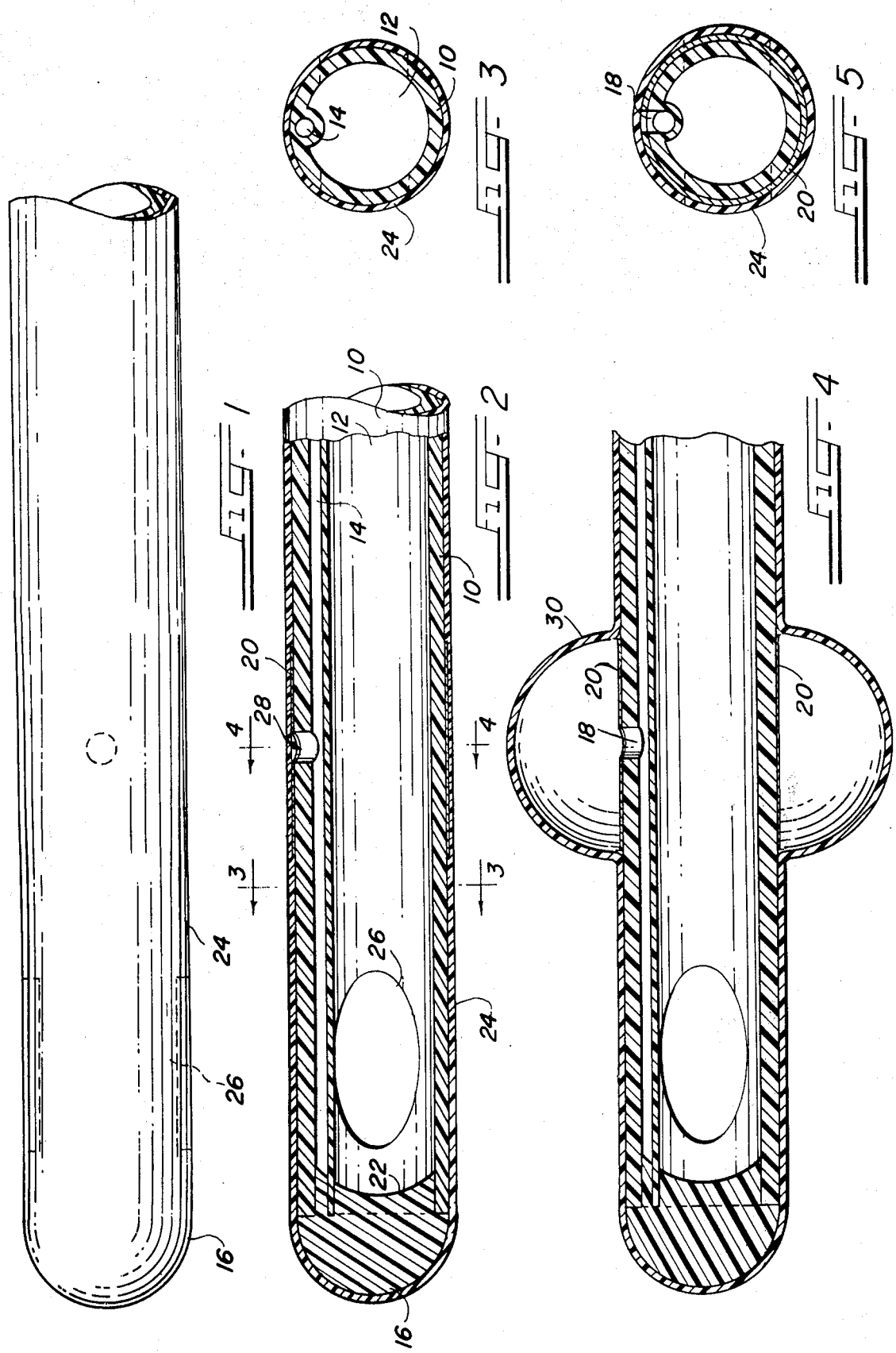

SILICONE CATHETER

This is a division of application Ser. No. 491,623, filed July 25, 1974 now U.S. Pat. No. 3,926,705.

BACKGROUND

The present invention concerns improvements in a silicone catheter, a tubular medical device for insertion into the body for the purpose of injecting or withdrawing fluids. Although the invention is described in the following specification with particular reference to a Foley catheter for insertion in the urethra, the invention is equally applicable to similarly constructed medical devices such as endotracheal tubes, tracheal tubes, Dennis tubes (used for decompressing the intestinal tract prior to or after gastrointestinal surgery), rectal catheters, Trocar catheters, hematuria balloon cateters, heart catheters, and others. In addition, the concepts of this invention could also be applied to similarly constructed non-medical devices.

The typical Foley catheter consists of a tube or shaft containing a primary lumen which is the conduit for removal or insertion of the appropriate fluid. Within this primary lumen and attached to the wall thereof is at least one secondary, smaller lumen which is the conduit for the injection of an appropriate gas or fluid for inflation of a balloon anchoring the catheter inside the patient. The anchoring balloon generally consists of a thin, elastic material extending around the exterior of the catheter near its tip and attached at its edges or shoulders to the exterior of the catheter. A hole in the tube wall permits the inflation gas or fluid to enter underneath the elastic material and expand it to a balloon-like configuration.

In use the catheter is inserted into the body cavity, and an inflation fluid is pumped through the secondary lumen to expand the anchoring balloon. This prevents accidental removal of the catheter from the patient and stations the catheter in the appropriate position for efficient use. Once the catheter is so anchored, body fluids can be drained or therapeutic fluids can be injected into the body through the primary lumen. When the catheter is no longer needed, the inflation balloon is deflated by releasing the inflation fluid or gas and the catheter is withdrawn from the body.

Although this basic design for a catheter has been used for a number of years, serious problems remain in the design and method of construction of these devices. In particular, there are problems with the previous methods which have been used to provide the elastic exterior portion which forms the anchoring bubble. For example, in U.S. Pat. No. 3,734,100 issued to Walker et al, a catheter construction is described in which a separate cuff portion is glued at its shoulders to the surface of the catheter. Although the patent illustrates the exterior surface of the catheter as being smooth and regular, unfortunately, in practice the thickness of the cuff portion and the effects of the glue cause surface irregularities at the cuff's shoulders. Thus, in a typical catheter produced by the process of Walker et al. the shoulders of the cuff will protrude beyond the remaining exterior surface of the catheter. This situation is undesirable because such irregularities impede the insertion or withdrawal of the catheter and increase the discomfort to the patient. In addition, such a catheter construction is generally not amenable to mechanized production, and manufacture of the catheters by hand causes additional imperfections and defects.

As an alternative, it has been suggested to cover the exterior of the catheter tube in the area underlying the bubble with a masking (release) material, coating the tip of the catheter including the bubble region with a flexible, inflatable material, and subsequently removing the underlying masking material. For example, in the patents to Harautuneian (U.S. Pat. No. 3,292,627 and 3,304,353) the use of a water soluble masking material is suggested. However, there are several problems with this design. First, in simultaneously removing the water soluble release material and inflating the anchoring bubble, difficulties in the dissolution of the release material frequently cause particles to become lodged in the inflation lumen preventing further expansion of the anchoring bubble. Similarly, as discussed in Harautuneian's U.S. Pat. No. 3,452,756, the masking layer may only dissolve in the localized area adjacent the hole to the inflation lumen. Thus, the anchoring bubble may expand preferentially in that area and cause localized pressure injurious to the body tissue. The same general type of system is shown in British Pat. No. 1,234,037--Steer et al.

Alternatively, U.S. Pat. No. 3,544,668 issued to Dereniuk illustrates the use of a gel as a masking layer beneath the anchoring balloon. Following the formation of the outer skin on the catheter, the gel layer is volatilized by heat. This method is difficult to practice because the outer covering of the catheter must be applied before the release coating has dried or is touched.

A further difficulty encountered with the prior art processes for manufacturing a catheter is that they are not applicable to the most useful catheter material, silicone. It has been found that silicone is more compatible with human tissue than previously used rubber and plastic materials and that the incidence of infection in the body tissues is appreciably reduced with silicone catheters. Although attempts have been made to apply silicone coatings over conventional catheter tube materials, silicone bonds poorly with the majority of these other materials. Accordingly, it is preferable to construct the entire catheter of silicone. Because of silicone's hydrophobic nature, however, it is difficult to apply coatings such as those in the Harautuneian and Dereniuk patents to silicone. Thus, in addition to the problems generally encountered with water soluble or volatile release coatings, a further defect is that these coatings are not useful in preparing silicone catheters.

In view of the foregoing, it is an object of the present invention to provide an improved catheter construction.

It is also an object of this invention to provide an improved silicone catheter and made entirely of silicone.

It is a further object of this invention to provide a catheter which does not suffer the defects of localized swelling of the anchoring bubble or the plugging of the inflation lumen caused by the particles from the release coating.

SUMMARY OF THE INVENTION

The invention comprises an improved catheter design.

The catheter comprises a tubular body comprising a larger primary lumen and a smaller inflation lumen; a smooth tip at the distal end of the catheter body which seals the primary and inflation lumens; an outer covering enclosing the tubular catheter body and the tip; the tubular catheter body containing a first hole to permit communication of fluids through the outer covering between the exterior of the tube and the primary lumen and a second hole permitting communication between the exterior of the tube and the inflation lumen but not through the outer covering; and a thin thermoplastic tape surrounding the tube underneath the outer covering and overlapping the second hole, the width of the tape corresponding to the desired base of the anchoring bubble formed by inflation of a portion of the outer layer, the tape containing a hole adjacent said second hole to permit the inflation of the anchoring bubble and the tape comprising a material to which said outer layer does not adhere.

DESCRIPTION OF THE DRAWINGS

The invention is illustrated by the following drawings in which FIG. 1 is a "top view" of the uninflated catheter.

FIG. 2 is a partially cutaway "side view" of the uninflated catheter.

FIG. 3 is a cross section of the uninflated catheter taken along line 3—3 of FIG. 2.

FIG. 4 is a cutaway "side view" of the catheter illustrating the inflated anchoring bubble.

FIG. 5 is a cross section of the uninflated catheter taken along line 4—4 of FIG. 2.

Referring to the drawings, the first step in the preparation of the catheter is the formation of tube 10 comprising primary lumen 12 and inflation lumen 14. The cross-sectional shape and orientation of these two channels may take various forms other than that shown in FIGS. 3 and 5. However, to provide the minimum amount of resistance for insertion into the patient, it is desirable that the exterior cross section of the tube be essentially round. Formation of this tube can be accomplished by an ordinary procedure, such as extrusion, wherein a continuous length of tubing is formed. The tubing is then cut to the appropriate length desired for the catheter.

After the tubular body of the catheter is formed, an inflation hole 18 is formed in the exterior of the tube to provide a passage to the inflation lumen. This hole is located at an appropriate distance from the distal end of the catheter tube where the anchoring bubble is to be located. The distal end of the catheter refers to the end which is inserted into the patient. The hole can be formed by any standard procedure, such as cutting or punching the exterior of the catheter tube.

Following the formation of the inflation hole a layer of thermoplastic material 20 is wrapped around the tube so that it covers the inflation hole. An appropriate thermoplastic material is a thermoplastic tape whose adhesive side adheres to the exterior of tube 10 but whose opposite side does not adhere to the subsequently applied outer layer of the catheter. The wrapping of the thermoplastic tape can be accomplished by hand or by mechanical means in such a manner that the ends of the tape overlap very slightly. This will insure that the outer covering which forms the anchoring bubble will not adhere to any portion of the underlying tube. In addition, the thermoplastic tape should be thin, for example less than 0.05 inch and, preferably, approximately 0.004 inch in thickness. This should avoid any impairment to the insertion of the catheter into the body caused by an enlargement of the outside diameter of the catheter tube in the region adjacent the thermoplastic tape.

Following the application of the thermoplastic tape a tip 16 is formed on the distal end of the catheter. Although the tip shown in the drawing is semi-spherical in shape, the actual configuration of the tip can take any form which facilitates the insertion of the catheter into the body. Preferably the tip is molded to the tubular body, for example, by placing the end of the tube into an open metal form filled with liquid material. This method of forming the tip is preferred, since it provides a secure seal of the inflation lumen at 22. Without such a seal it would be difficult, if not impossible, to inflate and maintain the anchoring bubble.

After these essential elements of the catheter are formed and assembled, an outer layer of material is applied over the length of the catheter by dipping the catheter into a solution of the covering material. The coating is dried and cured at room temperature and humidity over night or more rapidly at elevated temperatures. Additional coatings may be required to achieve the desired thickness of the outer layer. The procedures for dip coating a catheter with silicone are known to those skilled in the art as shown, for example, in U.S. Pat. No. 3,434,869, issued to Davidson. As illustrated in the drawings, the completed coated catheter has a smooth outer surface which does not present any protrusions which might impede the insertion or extraction of the catheter from the body.

Following the formation of the coating, hole 26 is punched in the catheter wall to provide a channel between the primary lumen and the exterior of the catheter. Although this hole can take any shape and size, as shown in the drawings, identical oval holes are punched on opposite sides of the catheter to facilitate injection or withdrawal of the fluids from the body.

Finally, an inflation hole 28 is formed in the thermoplastic tape. This hole is adjacent the inflation hole 18 previously cut in the wall of the catheter tube. The thermoplastic tape is pierced by touching the silicone coating over the opening 18 with a hot probe the temperature of which is adjusted to melt the thermoplastic tape but not to affect the silicone outer coating.

The advantages of the present invention are readily apparent from FIG. 4 which shows the anchoring bubble of the catheter in its inflated position. When the inflation fluid or gas is forced through inflation lumen 14, it inflates the bubble as shown in FIG. 4. Since the masking material does not have to be dissolved during inflation, the inflation occurs steadily and uniformly and the inflation lumen will not become plugged by particles of partially dissolved masking material.

As mentioned previously, it is desirable to build the entire catheter of silicone because of its compatibility with human tissues. Typically the tubular catheter body and the tip are made of much harder silicones than that used for the outer covering.

The thermoplastic masking tape may be made of any thin material whose adhesive side adheres to the tubular body of the catheter, whose opposite side does not adhere to the outer coating of the catheter, and which melts at a temperature significantly lower than that of the outer coating. Where the tubular body and outer coating are both made from silicone, a suitable release material consists of unreinforced polyethylene or polypropylene tape having a thickness of approximately 0.005 inch.

Typical properties of materials presently available which are suitable for use in the present invention are designated in Table I.

TABLE I

|  | Tubular Body | Tip | Outer Coating |
|---|---|---|---|
| Shore A Durometer | 50–70 | 30–70 | 30–55 |
| Tensile Strength (p.s.i.) | 900–1400 | 850–1200 | 300–900 |
| Elongation (%) | 200–500 | 125–900 | 350–800 |
| Tear Resistance (lbs./in.) | 60–200 | 20–100 | 40–130 |
| Type of Silicone Rubber | Heat Cured* | 2 Part Room** Temperature Vulcanizing | 1 Part Room*** Temperature Vulcanizing |

*Cured at elevated temperature and pressure in the presence of peroxide.
**Mixed with a catalyst, normally a metallic soap, and cured at room temperature.
***Cured by exposure to moist air at room temperature.

Following the formation of the catheter illustrated in the drawings it is also desirable to mold to the external end of the catheter suitable apparatus containing a provision for injecting gas or fluid into the inflation lumen and for connecting the primary lumen to suitable drainage or injection means. A typical device is shown, for example, in U.S. Pat. No. 3,769,981 to McWhorter et al.

EXAMPLE

A silicone catheter was prepared according to the following procedure. First, a silicone mixture was prepared using the heat cured silicone rubber described in Table II and 1.0 percent of a catalyst comprising bis 2-4 dichlorobenzoyl peroxide (Cadox TS-50). This mixture was extruded into a tube comprising a primary lumen and an inflation lumen arranged as shown in FIGS. 1 through 5. This tube is extruded through a tunnel maintained at about 900°F and has a residence time within the tunnel of approximately 1-4 minutes. As the tube leaves the tunnel it is cut to the size appropriate for the particular application of the catheter. Subsequently, a hole is punched at the distal end of the tubular body of the catheter at the location of the anchoring balloon, the hole providing a passage to the inflation lumen.

At this point the tip is formed on the distal end of the catheter. A liquid two-part silicone rubber (as described in Table II) is poured into a steel mold, and the distal end of the catheter is immediately inserted into the mold. The catheter is permitted to remain in the mold while the silicone tip is cured. The catheter is removed from the mold and cured for 4 hours at 350°F. This process drives off any remaining catalyst and completes the cure of the catheter body.

The catheter is prepared for dip coating by applying a strip of polypropylene tape around the catheter tube so that it overlaps the previously punched hole. The catheter is then dipped into a 40 percent solvent solution one-part room temperature vulcanized silicone rubber (as described in Table II) and cyclohexane, withdrawn at a slow, steady rate, inverted and dried for 40 minutes at 120°F. This dipping and drying procedure is repeated two additional times. On the final (third) coating blue dye is added to the silicone solution to add color to the catheter.

Following the final drying step, two elliptical drainage holes are punched in the distal end of the catheter to provide communication of the drainage lumen with the exterior of the catheter. A probe heated to 500°F is then applied for about 30 seconds to the catheter skin adjacent the hole to the inflation lumen to form a hole in the polypropylene tape.

The catheter is tested by inflating and inspecting the anchoring balloon.

TABLE II

|  | Tubular Body | Tip | Outer Coating |
|---|---|---|---|
| Shore A Durometer | 60±5 | 35±5 | 40±5 |
| Tensile Strength (p.s.i.) | 1100 | 925 | 800 |
| Elongation (%) | 350 | 150 | 700 |
| Tear Resistance (lbs./in.) | 90 | 25 | 100 |
| Type of Silicone Rubber | Heat Cured | 2 Part Room Temperature Vulcanizing | 1 Part Room Temperature Vulcanizing |

It should be mentioned that the order of the foregoing steps in the process of producing the catheter of this invention may be varied from that described without any effect on the catheter. For example, the tip may be molded to the body before application of the masking tape and the order of forming holes 26 and 28 may be reversed.

I claim:
1. In a catheter comprising:
   1. a tubular body comprising a primary lumen and an inflation lumen;
   2. a smooth tip at the distal end of said tubular catheter body;
   3. an outer covering enclosing said tubular catheter body and said tip;
   4. said tubular body containing a first hole to permit communication through said outer covering between the exterior of said tube and said primary lumen and a second hole permitting communication between the exterior of said tube and said inflation lumen but not through said outer covering, the improvement comprising: a thin layer of thermoplastic material surrounding said tube underneath but not adhering to said outer covering and overlapping said second hole, the width of said layer of material corresponding to the desired base of an anchoring bubble formable by inflation of a portion of the outer layer, said layer of thermoplastic material containing a hole in communication with said second hole to permit said inflation, said thermoplastic material having a melting point lower than said outer covering whereby said hole in the thermoplastic material may be formed by application of heat to the overlying outer covering.

2. The catheter of claim 1 wherein said outer layer is formed of silicone.

3. The catheter of claim 2 wherein said tubular body and said smooth tip are formed of silicone.

4. The catheter of claim 1 wherein the layer of thermoplastic material is unreinforced tape of a member selected from the group consisting of polyethylene and polypropylene.

5. The catheter of claim 4 wherein said outer layer presents a smooth exterior surface for contacting body tissues without any protrusions or other variations which would interfere with the easy insertion of said catheter into the body.

* * * * *

UNITED STATES PATENT OFFICE
CERTIFICATE OF CORRECTION

PATENT NO. : 3,983,879

DATED : October 5, 1976

INVENTOR(S) : Donald A. Todd

It is certified that error appears in the above–identified patent and that said Letters Patent are hereby corrected as shown below:

Column 1, lines 17-18, "caterers" should be -- catheters --;
Column 2, line 53, delete "and";
Column 3, line 37, "an" should be -- any --;
Column 5, Table I, "1 Part Room**" should read
         -- 1 Part Room*** --;
Column 6, Claim 1, subparagraphs "1.", "2.", "3.", and "4."
         should be designated -- (1) --; -- (2) --;
         -- (3) --;. and -- (4) -- to distinguish
         these subparagraphs of Claim 1 from the
         remaining claims.

Claim 1, subparagraph 4, lines 38, 40 and 43, "tube"
         should be -- tubular body --.

Signed and Sealed this

Fifth Day of April 1977

[SEAL]

Attest:

RUTH C. MASON
Attesting Officer

C. MARSHALL DANN
Commissioner of Patents and Trademarks